(12) United States Patent
Wang et al.

(10) Patent No.: US 9,763,944 B2
(45) Date of Patent: Sep. 19, 2017

(54) METHOD OF OPTIMIZING THE TREATMENT OF PROLIFERATIVE DISEASES MEDIATED BY THE TYROSINE KINASE RECEPTOR KIT WITH IMATINIB

(71) Applicants: Yanfeng Wang, Florham Park, NJ (US); Elisabeth Wehrle, Efringen-Kirchen (DE)

(72) Inventors: Yanfeng Wang, Florham Park, NJ (US); Elisabeth Wehrle, Efringen-Kirchen (DE)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 15/297,372

(22) Filed: Oct. 19, 2016

(65) Prior Publication Data
US 2017/0035757 A1 Feb. 9, 2017

Related U.S. Application Data

(63) Continuation of application No. 14/924,207, filed on Oct. 27, 2015, now abandoned, which is a continuation of application No. 12/863,627, filed as application No. PCT/US2009/031510 on Jan. 21, 2009, now abandoned.

(60) Provisional application No. 61/022,945, filed on Jan. 23, 2008.

(51) Int. Cl.
*A01N 43/00* (2006.01)
*A61K 31/33* (2006.01)
*A61K 31/506* (2006.01)
*G01N 33/574* (2006.01)

(52) U.S. Cl.
CPC ..... *A61K 31/506* (2013.01); *G01N 33/57446* (2013.01)

(58) Field of Classification Search
None
See application file for complete search history.

(56) References Cited

U.S. PATENT DOCUMENTS

| 2004/0054186 | A1 | 3/2004 | Das et al. | |
| 2005/0049268 | A1* | 3/2005 | Mahon | A61K 8/4953 514/275 |
| 2006/0019280 | A1* | 1/2006 | Chen | C07K 14/715 435/6.16 |
| 2007/0213317 | A1* | 9/2007 | Buchdunger | A61K 31/502 514/211.09 |

FOREIGN PATENT DOCUMENTS

| WO | 2006121941 A2 | 11/2006 |
| WO | 2008036792 A2 | 3/2008 |
| WO | 2008061622 A1 | 5/2008 |
| WO | WO 2008061622 A1 | 5/2008 |

OTHER PUBLICATIONS

Perik et al., "Results of plasma N-terminal pro B-type natriuretic peptide and cardiac troponin monitoring in GIST patients do not support the existence of imatinib-induced cardiotoxicity," Ann Oncol (2007).*
Verweij et al., "Progression-Free Survival in Gastrointestinal Stromal Tumours with High-Dose Imatinib: Randomised Trial," Lancet, Sep. 25, 2004, vol. 364: 1127-1134.*
Manley et al., "Imatinib: A Selective Tyrosine Kinase Inhibitor," European Journal of Cancer, vol. 38, Suppl. 5 (2002) S19-S27.*
Demetri et al., "Imatinib plasma levels are correlated with clinical benefit in patients with unresectable/metastatic gastroinestinal stromal tumors," Journal of Clinical Oncology, vol. 27, No. 19, Jul. 1, 2009.*
ASCO GI: "Serum Imatinib (Gleevec) Levels GIST Response" MedPage Today, Jan. 25, 2008.
F. Lowry "Imatinib plasma Levels Linked to Clinical Benefit in Gastrointestinal Stromals Tumors" Elsevier Global Medical News, Jan. 28, 2008.
Peng Bin et al., "Clinical Pharmacokinetics of Imatinib", Clinical Pharmacokinetics, pp. 879-894, 2005.
Widmer et al., "Determination of imatinib Gleevec in human plasma by . . . ", Journal of Chromatography, pp. 285-292, Apr. 25, 2004.
Peng et al., "Pharmacokinetics & pharmacodynamics of imatinib in a phase I trial with chronic myeloid leukemia patients", Journal of Clinical Oncology, pp. 935-942, 2004, Mar. 1, 2004.
Manley et al., "Imatinib: a selective tyrosine kinase inhibitor", European Journal of Cancer, vol. 38, Suppl. 5, S19-S27, 2002.
Verweij et al., "Progression-Free Survival in Gastrointestinal Stromal Tumours with High-Dose Imatinib: Randomised Trial," Lancet, Sep. 25, 2004, vol. 364: 1127-1134, 2004.
Picard et al., "Trough Imatinib Plasma Levels are Associated with Both Cytogenetic and Molecular Responses to 2007Standard-Dose Imatinib in Chronic Myeloid Leukemia," Blood, vol. 109, No. 8, Apr. 15, 2007.
Blood, vol. 108, No. 11, Part 1, p. 131a, 2006.
Shin Yakuzai-gaku Souron (New General Pharmaceutics) (the 3rd revised edition), Nankodo Co. Ltd., pp. 250-252, 1987.
Perik et al., "Results of plasma N-terminal pro B-type natriuretic peptide and cardiac troponin monitoring in GIST patients do not support the existence of imatinib-induced cardiotoxicity", Ann Oncol, pp. 1-3, (2007) (first published online Oct. 24, 2007).
Vaidyanathan S. et.al.: "Lack of pharmacokinetic interactions of aliskiren, a novel direct renin inhibitor for the treatment of hypertension, with the antihypertensives amlodipine, valsartan, hydrochlorothiazide (HCTZ) and ramipril in healthy volunteers" International Journal of Clinical Practice Nov. 2006, LNKD-PUBMED. 17073832, vol. 60, No. 11, Nov. 2006 pp. 1343-1356, XP002594084ISSN: 1368-5031.
Anonymous: "An assessment of long term safety of the combination of Aliskiren/amlodipine in patients with high blood pressure" clinical trials.gov Dec. 8, 2006, XP002594286 retrieved from the internet: URL:http:// clinicaltrials.gov/archive/NCT004021 Mar. 2006 12 08 [retrieved on Jul. 29, 2010].
Nishida T., "Gastrointestinal stromal tumor (GIST)", Geka (Surgery), Nankodo Co., Ltd, 2005, vol. 67, No. 4, pp. 412-418 (English Translation).
"Yakabutu-gaku (Pharmacology)", Nanzanado Co., Ltd., 1984, pp. 30-31 (English translation).

* cited by examiner

*Primary Examiner* — Jared D Barsky
(74) *Attorney, Agent, or Firm* — Michelle Han

(57) ABSTRACT

The invention relates to a method of treating proliferative diseases mediated by the tyrosine kinase receptor KIT, in particular GIST, in a human patient population.

3 Claims, 1 Drawing Sheet

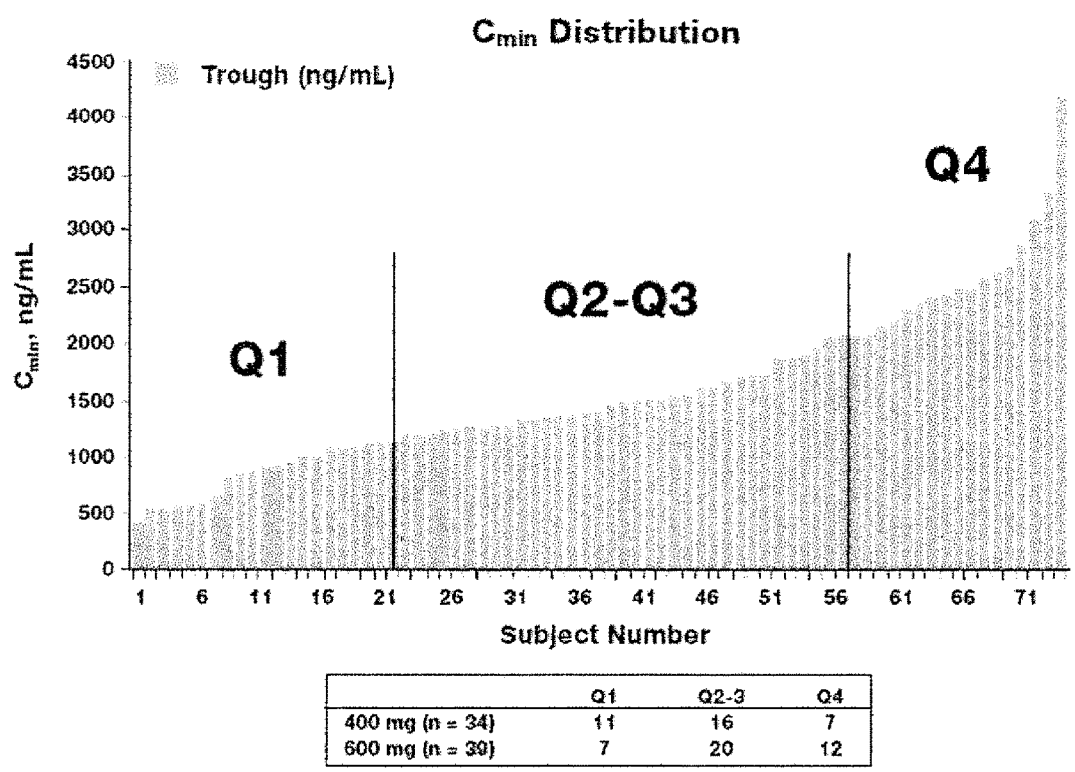

METHOD OF OPTIMIZING THE TREATMENT OF PROLIFERATIVE DISEASES MEDIATED BY THE TYROSINE KINASE RECEPTOR KIT WITH IMATINIB

The present invention relates to a method of treating proliferative diseases mediated by the tyrosine kinase receptor KIT, in particular gastro-intestinal stromal tumors (GIST), in a human patient population.

GIST are uncommon visceral sarcoma that arise predominantly in the gastrointestinal tract. GIST are the most common subtype of GI sarcomas, which also include leiomyosarcomas, liposarcomas and other more rare histologic subtypes. GIST have been reported to represent about 3% of all malignant tumours. GIST are most common in the stomach (60 to 70%), followed by small intestine (20-30%).

Recent advances in molecular and immunohistochemical analysis of GIST have identified that GIST cells are positive for CD117, a cell surface antigen localised on the extracellular domain of the trans-membrane tyrosine kinase receptor KIT, the protein of the proto-oncogene c-KIT and receptor for stem cell factor. Upon binding its ligand, stem cell factor, KIT forms a dimer that is autophosphorylated and activates signaling cascades that lead to cell growth. Mutations that lead to an activated form of KIT, especially forms that are activated independently of its ligand, are known and are believed to play a role in certain proliferative diseases, such as mast cell diseases, like mastocytosis, particularly systemic mastocytosis, acute myelogenous leukemia, GIST, sinonasal NK/T-cell lymphoma, seminomas and dysgerminomas. It is hypothesized that virtually all malignant GIST harbour mutations of c-KIT as the driving factor of this disease, resulting in constitutive activation of KIT associated with the signal transduction pathway for cell division and tumour growth. KIT overexpression is determined by immunohistochemistry, which is performed in standard practice.

The present invention relates to a method for minimizing or avoiding the issues of tolerability, lack of efficacy and the risk of relapse in human patients suffering from a proliferative disease mediated by the tyrosine kinase receptor KIT. The invention is based on the finding that the treatment of a proliferative disease, which is mediated by the tyrosine kinase receptor KIT, comprising the administration of a KIT inhibitor or a pharmaceutically acceptable salt thereof to a patient suffering from such proliferative disease can be optimized by adjusting the dose of the KIT inhibitor or a pharmaceutically acceptable salt thereof applied to an individual patient in a manner that a specific minimum plasma trough level (Cmin) of the KIT inhibitor is achieved in each single patient. It was found that an individual adjustment for each patient is often required in view of high patient intervariability of the Cmin values after administration of KIT inhibitor to each patient.

The term "proliferative disease mediated by the tyrosine kinase receptor KIT" as used herein should include mast cell diseases, such as mast cell leukemia and systemic mastocytosis, acute myelogenous leukemia (AML), GIST, seminomas, dysgerminomas and metastatic melanoma. The term "proliferative disease mediated by the tyrosine kinase receptor KIT" means especially the proliferative disease systemic mastocytosis, particularly aggressive systemic mastocytosis and GIST, more specifically GIST.

The term "KIT inhibitor" as used herein means a therapeutically active compound such as a small organic molecule or an antibody, which inhibits the activity of the tyrosine kinase receptor KIT, more specifically wild type KIT and certain KIT mutations as defined below. Preferably, the KIT inhibitor inhibits preferably KIT harboring activating mutations.

In one embodiment, the KIT inhibitor employed in the present invention is Imatinib, which has the structure of formula (I),

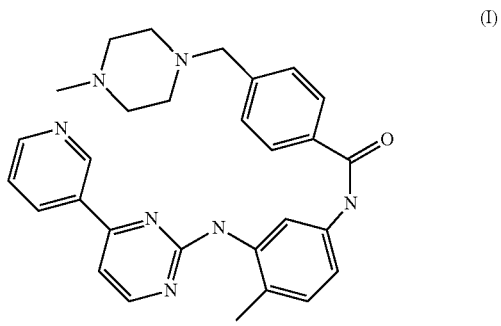 [SMILES: Cc1ccc(NC(=O)c2ccc(CN3CCN(C)CC3)cc2)cc1Nc1nccc(-c2cccnc2)n1]

hereinafter "Compound (I)", or a pharmaceutically acceptable salt thereof. Imatinib is a tyrosine kinase inhibitor that selectively inhibits wild type KIT and certain KIT mutations. In February 2002 the mesylate salt of N-{5-[4-(4-methyl-piperazino-methyl)-benzoylamido]-2-methylphenyl}-4-(3-pyridyl)-2-pyrimidine-amine (Imatinib mesylate, STI571, Glivec®) was approved by the FDA for the treatment of adult patients with CD117 positive unresectable and/or metastatic malignant GIST.

In another embodiment, the KIT inhibitor employed in the present invention is Nilotinib or a pharmaceutically acceptable salt thereof. Nilotinib is a tyrosine kinase inhibitor that selectively inhibits KIT. In 2007 the monohydrochloride monohydrate salt of 4-methyl-3-[[4-(3-pyridinyl)-2-pyrimidinyl]amino]-N-[5-(4-methyl-1H-imidazol-1-yl)-3-(trifluoromethyl)-phenyl]benzamide (Nilotinib monohydrochloride monohydrate, Tasigna®), which has the structure (II), hereinafter "Compound (II)",

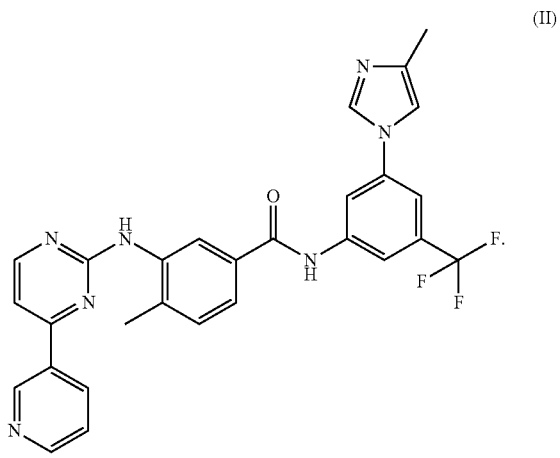 [SMILES: Cc1cn(-c2cc(NC(=O)c3ccc(C)c(Nc4nccc(-c5cccnc5)n4)c3)cc(C(F)(F)F)c2)cn1]

was approved by the FDA for the treatment of CML for patients who are resistant or intolerant to existing therapies, including treatment with Glivec®. The compound of formula (II) and the process for its manufacture are disclosed in U.S. Pat. No. 7,169,791, which is hereby incorporated into the present application by reference.

Mutations that lead to an activated form of KIT as referred to herein include, but are not limited to D816F, D816H, D816N, D816Y, D816V, K642E, Y823D, Del 550-558, Del 557-561, N822K, V654A, N822H, Del 650-558+V654A, Del 557-561+V654A, Ins503AY, V560G, 558NP, Del 557-558, Del VV559-560, F522C, Del 579, R634W, K642E, T801I, C809G, D820Y, N822K, N822H, Y823D, Y823C and T670I.

The present invention provides for the first time an individualized treatment schedule for single patients suffering from a proliferative disease mediated by the tyrosine kinase receptor KIT based on a Cmin lower threshold which was shown to be correlated with an increased overall response (OR) rate and an increased time to progression (TTP).

The term "disease mediated by the tyrosine kinase receptor KIT" as used herein means a disease, wherein KIT is activated by mutations or other molecular mechanisms or overexpressed, in particular to GIST and systemic mastocytosis, more preferably GIST.

In particular, it was found that patients suffering from GIST having Imatinib levels below about 2050 ng/mL, more specifically, Imatinib levels below about 1100 ng/mL, show lower OR rate and shorter TTP than patients above that threshold.

As mentioned before, GIST belongs to the group of disease mediated by the tyrosine kinase receptor KIT. The results obtained with the GIST patient population described herein can be transferred directly to the whole group of disease mediated by the tyrosine kinase receptor KIT.

The term "method of treatment" as used herein relates also to a method of prevention of the diseases mentioned herein, i.e. the prophylactic administration of a pharmaceutical composition comprising a KIT inhibitor to healthy patients to prevent the development of the diseases mentioned herein.

The terms "adjusting the dose" and "the dose of . . . is adjusted" as used herein preferably denote that the dose referred to is increased or decreased. In a broader sense of the invention, the terms "adjusting the dose" and the "dose of . . . is adjusted" encompass a situation wherein the dose remains unchanged.

Hence, in one aspect, the present invention pertains to a method of treating a proliferative disease mediated by the tyrosine kinase receptor KIT, in a human patient comprising the steps of
(a) administering a predetermined fixed amount of Imatinib or a pharmaceutically acceptable salt thereof, e.g. an oral daily dose 400 mg or 600 mg of the monomesylate salt of Imatinib, to the human patient suffering such disease,
(b) collecting at least one blood sample from said patient, e.g. within the first 12 months of treatment, e.g. within the first 30 days,
(c) determining the Cmin of Imatinib, and
(d) adjusting the dose of Imatinib or a pharmaceutically acceptable salt thereof in a manner that a Cmin of at least 1100 ng/mL . . . , preferably a Cmin between 1100 and about 2500 ng/mL, of Imatinib is achieved in said patient.

In a broader sense, the present invention provides a method of treating a proliferative disease mediated by the tyrosine kinase receptor KIT in a human patient wherein the dose of Imatinib or a pharmaceutically acceptable salt thereof is adjusted in a manner that a Cmin of at least 1100 ng/mL, especially between about 1100 and about 2500 ng/mL, preferably a Cmin between 2050 and about 2500 ng/mL, of Imatinib is maintained in said patient.

More specifically, the present invention relates to a method of treating GIST in a human patient comprising the steps of
(a) administering a predetermined fixed amount of Imatinib or a pharmaceutically acceptable salt thereof to the human GIST patient in need thereof,
(b) collecting at least one blood sample from said patient, e.g. within the first 12 months, especially the first 3 months, more especially the first 30 days, of treatment,
(c) determining the plasma trough level (Cmin) of Imatinib, and
(d) adjusting the dose of Imatinib or a pharmaceutically acceptable salt thereof in a manner that a Cmin of at least 1100 ng/mL, especially between about 1100 and about 2500 ng/mL, preferably a Cmin between 2050 and about 2500 ng/mL, of Imatinib is achieved in said patient.

In one embodiment of the present invention, the predetermined fixed amount referred to herein under step (a) represents a therapeutically effective amount.

Throughout the present invention, preferably the monomesylate salt of Imatinib is used in step (a), e.g. in an oral daily dose of between about 200 and about 800 mg, preferably in a daily dose of about 400 or 600 mg.

Another important aspect of the present invention is the use of Imatinib or a pharmaceutically acceptable salt thereof, especially Imatinib mesylate, for the manufacture of a medicament for the treatment of GIST, wherein the dose of the pharmaceutically acceptable salt is adjusted in a manner that a Cmin of at least 1100 ng/mL, especially between about 1100 and about 2500 ng/mL, preferably a Cmin between 2050 and about 2500 ng/mL, of Imatinib is maintained in said patient.

The present invention is in particular of benefit for patients with GIST harboring the exon 11 KIT mutation. For the latter sub-population the OOR was 67% for patients with a Cmin below 1100 ng/mL compared to 100% for patients with a Cmin above 1100 ng/mL.

The compounds of formula us specifically disclosed in the patent applications U.S. Pat. No. 5,521,184, in particular in Example 21, the subject-matter of which is hereby incorporated into the present application by reference, Imatinib can also be prepared in accordance with the processes disclosed in WO03/066613.

For the purpose of the present invention, Imatinib is preferably applied in the form of its mono-mesylate salt. Imatinib mono-mesylate can also be prepared in accordance with the processes disclosed in U.S. Pat. No. 6,894,051 the subject-matter of which is hereby incorporated into the present application by reference. Comprised are likewise the corresponding polymorphs, e.g. crystal modifications, which are disclosed therein.

In step (a) of the method described above, in particular a daily dose of between about 200 and about 800 mg, e.g. 400 mg, of the mono-mesylate salt of Imatinib is administered orally. Imatinib mono-mesylate can be administered in dosage forms as described in U.S. Pat. Nos. 5,521,184, 6,894,051, US 2005-0267125 or WO2006/121941.

The collecting of a blood sample from patients required under the methods described herein can be accomplished by standard procedures being state of the art. A suitable procedure for the determination of the plasma trough level Cmin of Imatinib and N-{5-[4-(piperazinomethyl)-benzoylamido]-2-methylphenyl}-4-(3-pyridyl)-2-pyrimidine-amine was described by R. Bakhtiar R et al. in J Chromatogr B Analyt Technol Biomed Life Sci. 2002 Mar. 5; 768(2): 325-40.

SHORT DESCRIPTION OF THE FIGURES

FIG. 1 depicts the Imatinib trough distribution of the study described in Example 1 (400 mg and 600 mg data combined).

EXAMPLE 1

Imatinib Pharmacokinetics (PK) and its Correlation with Clinical Response in Patients with Unresectable/Metastatic Gastrointestinal Stromal Tumor (GIST)

PURPOSE: In the randomized Phase II study (B2222), 147 pts with unresectable/metastatic GIST were randomized 1:1 to receive imatinib (IM) at 400 vs 600 mg daily. Fifty-two (52%) percent of patients are alive for >5 years, regardless of initial dose level. We report the pharmacokinetics (PK) of imatinib (IM) and the relationship between IM levels and clinical response.

METHODS: The IM plasma levels were analyzed in a subset of patients (n=73) for whom PK data on day 1 and at steady state (Day 29) was available (n=34 and 39 for 400 and 600 mg/day, respectively). The effect of patients demographics and blood chemistry parameters on IM PK was evaluated using a population PK approach. A relationship between IM plasma exposure and clinical outcome was explored by grouping patients into quartiles according to IM trough levels (Cmin). The clinical outcome parameters evaluated include overall objective responses (OOR=CR+PR+SD), time to progression (TTP), and KIT mutations.

RESULTS: Population PK analysis showed that patients age, gender, and BW had little effect on imatinib clearance, whereas plasma albumin and WBC counts at baseline were identified as significant covariates. Patients with a higher albumin level or lower WBC counts at baseline appeared to have a higher clearance for IM. Clinical outcomes appeared to be correlated with IM trough exposure. OOR was achieved by 12 of 18 (67%) patients in Q1 (Cmin<1110 ng/mL) compared with 29 of 36 (81%) and 16 of 19 (84%) in Q2-Q3 (≥1110-<2040 ng/mL), and Q4 (≥2040 ng/mL), respectively (p=0.177 for Q1 vs Q2-Q4). The median TTP was 11.3 months for patients in Q1 and over 30 months for Q2-Q4 (p=0.0029). In patients with Exon 11 KIT mutations (n=39), the OOR was 67% for Q1 vs 100% for Q2-Q4 (p=0.009). Exon 9 KIT mutation was found in only 12 patients with Cmin data, limiting the power of any correlative analyses in this subset. The IM plasma AUC, peak concentration, and Cmin were highly correlated, with IM Cmin having the best correlation with response.

CONCLUSION: IM demonstrated good oral absorption, but large inter-patient variability in IM exposure. Patients with the lowest IM trough levels (<1100 ng/mL) show lowest OOR rate and shortest TTP.

The invention claimed is:

1. A method of selectively treating a patient having unresectable/metastatic GIST harboring the Exon 11 KIT mutation, said method comprising:
    (a) administering a predetermined fixed dose of 400 mg or 600 mg of imatinib mesylate to the patient;
    (b) obtaining at least one blood sample from the patient within the first 12 months of treatment;
    (c) detecting a plasma trough level (Cmin) of less than 1100 ng/mL in the blood sample of the patient; and
    (d) thereafter selectively adjusting the dose of imatinib mesylate in a manner that maintains a Cmin of between 1100 and 2040 ng/mL of imatinib mesylate in the patient.

2. The method according to claim 1 wherein the at least one blood sample is collected within the first 3 months of treatment.

3. The method according to claim 1 wherein the at least one blood sample is collected within the first 30 days of treatment.

* * * * *